(12) United States Patent
Becca et al.

(10) Patent No.: US 9,042,521 B2
(45) Date of Patent: May 26, 2015

(54) BEAM LIGHTING UNIT FOR RADIOGRAPHIC APPARATUS

(71) Applicants: Antonio Becca, Imola (IT); Davide Bianconi, Castel Guelfo di Bolonga (IT); Dario Righini, Imola (IT)

(72) Inventors: Antonio Becca, Imola (IT); Davide Bianconi, Castel Guelfo di Bolonga (IT); Dario Righini, Imola (IT)

(73) Assignee: CEFLA SOCIETA COOPERATIVA (IT)

( * ) Notice: Subject to any disclaimer, the term of this patent is extended or adjusted under 35 U.S.C. 154(b) by 157 days.

(21) Appl. No.: 13/774,764

(22) Filed: Feb. 22, 2013

(65) Prior Publication Data
US 2013/0251109 A1 Sep. 26, 2013

(30) Foreign Application Priority Data
Mar. 21, 2012 (IT) .............................. BO2012A0153

(51) Int. Cl.
*G21K 1/04* (2006.01)
*A61B 6/06* (2006.01)

(52) U.S. Cl.
CPC .... *G21K 1/04* (2013.01); *A61B 6/06* (2013.01)

(58) Field of Classification Search
CPC .................................... G21K 1/04; A61B 6/06
USPC ................................................... 378/150, 156
See application file for complete search history.

(56) References Cited

U.S. PATENT DOCUMENTS

| | | | |
|---|---|---|---|
| 5,406,611 A | 4/1995 | Schobert | |
| 2002/0126799 A1* | 9/2002 | Saladin et al. | 378/152 |
| 2004/0234034 A1* | 11/2004 | Godzinsky | 378/145 |
| 2005/0152499 A1 | 7/2005 | Zhao | |
| 2006/0203966 A1* | 9/2006 | Mollus et al. | 378/150 |

FOREIGN PATENT DOCUMENTS

WO 02097827 12/2002

\* cited by examiner

*Primary Examiner* — Glen Kao
(74) *Attorney, Agent, or Firm* — Cooper & Dunham LLP

(57) ABSTRACT

Method for limiting an X-ray beam, wherein the X-ray beam is limited by a limiting unit comprising a couple of blades approaching each other or moving away from each other to adjust the width of a space between the blades the two blades being driven by an actuator (12) linked to both blades. The position of a symmetry axis (S) of the space between the blades is set in a shifting step by changing the distance between the blades and by impeding the motion of one blade in comparison with the motion of the other blade resulting in an asymmetric motion of the blades with respect to an initial position of the symmetry axis (S). The desired width (W) of the space between the blades is set in an adjustment step by an unimpeded symmetric motion of the blades with respect to the position of the symmetry axis (S) set in the shifting step.

10 Claims, 5 Drawing Sheets

BEAM LIGHTING UNIT FOR RADIOGRAPHIC APPARATUS

BACKGROUND OF THE INVENTION

The present invention relates to the technical field of radiology, and especially to beam limiting units used to define the shape of the X-ray beam emitted by an X-ray tube during the acquisition of a radiography.

The X-ray tube generally emits an X-ray beam, which is limited by beam stops near the X-ray source to a generally conical or pyramidal form. The beam is then further modified to obtain a final shape, which is defined downstream the emission point by guiding the X-ray beam through an aperture allowing it to get the desired shape and dimensions with greater precision. Usually with the passage through the aperture the X-ray beam assumes a square or rectangular shape.

In the different types of radiological acquisition, apertures having different shapes and dimensions must be interposed between the X-ray source and the X-ray detector, with the aim of conferring to the X-ray beam the shape and the dimensions optimal for that particular acquisition.

The use of beam limiting units is well known in the art, and in particular the use of beam limiting units which use one or more blades which can be moved in different ways through suitable actuators. These beam limiting units sometimes also form part of a collimator.

Typically a beam limiting unit is made of two blades and one or two actuators moving the blades. In this way, an aperture having a fixed height (corresponding to the blades height) and variable width (the distance between the internal edge of the two blades) is obtained. Superimposing perpendicularly two beam limiting units, an aperture having variable height and width can be obtained. The superimposition of two beam limiting units is known in the art.

The central rays of the final X-ray beam that has passed through the aperture must be in the desired position. One of the limits of prior art is the impossibility of setting the central ray of the final X-ray beam where desired, due to limitations linked to blades position. For instance, in the beam limiting unit known from DE 32 36 082 A1, the two blades move in a symmetrical way with respect to the central ray, which, once fixed, cannot be moved.

SUMMARY OF THE INVENTION

It is an object of the present invention to provide a collimation unit capable of forming an aperture having the desired width and the central ray of the X-ray beam leaving the aperture at a desired position, which might differ from the position of the central ray of the X-ray beam impinging on the aperture. It is moreover an object of the present invention to provide a beam limiting unit settable in a short time, and which, by reducing the number of electronically actuated components, is more reliable and easier to control, and which can finally be produced at low costs.

With respect to prior art beam limiting units which make use of an actuator for each blade (four blades and four actuators), the present invention has the advantage of a reduction of the actuators number, in that, with two actuators only, an aperture having the desired height and width can be obtained, and moreover having the central ray of the X-ray beam in the desired position. This is possible thanks to the particular movement, which allows first to move the blades to define the position of the axis of symmetry of the aperture, and thereafter to open or close them, so as to obtain a final X-ray beam having the desired shape and position. Due to the fact that both blades are directly linked to the actuator by separate force transmission chains, the actuator exerts force on both blades simultaneously resulting in both a speedy positioning of the central beam and a swift adjustment of the width.

Another advantage of the present invention lies in the possibility of moving the central ray of the final X-ray beam with respect to the central ray of the X-ray beam impinging on the aperture. This concept will be better explained in the following with the help of FIG. 3.

A further advantage of the present invention lies in the fact that the opening and closing of the aperture can occur even during the X-ray emission by the X-ray tube, which can be important in order to reduce the radiation dose to the patient. Imagine for instance to use the beam limiting unit during the acquisition of a panoramic radiography wherein initially a first condyle is irradiated, then the cranial frontal portion and finally the second condyle. When incisive teeth are irradiated, reducing the vertical dimension of the X-ray beam could be very useful, so as to avoid irradiating a radiosensitive tissue as retina.

It will be only briefly mentioned that the blades are made of material able to stop X-rays.

BRIEF DESCRIPTION OF THE DRAWINGS

The present invention will now be described in one of its embodiments with the help of the following figures, showing.

DETAILED DESCRIPTION OF THE INVENTION

Figure 1:
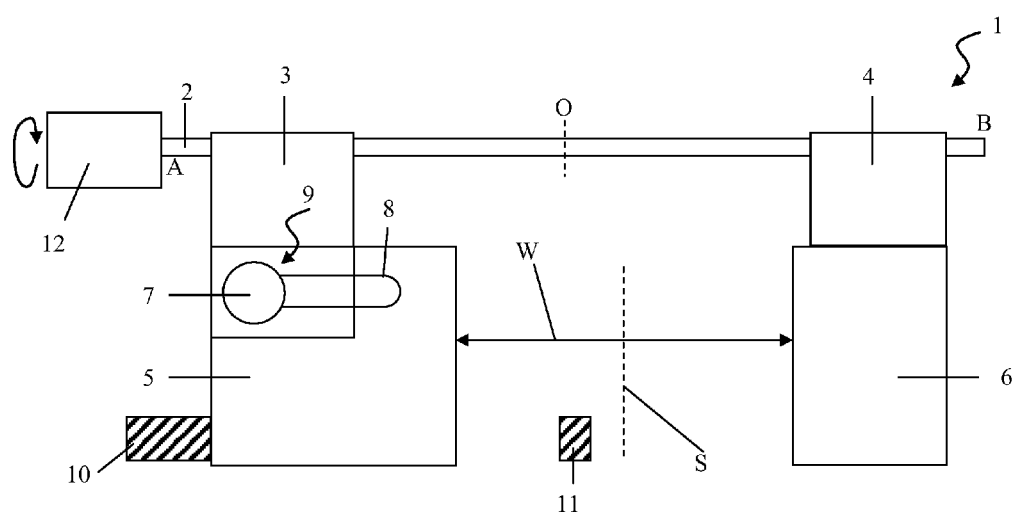
FIG. 1 a schematic view of the beam limiting unit of the present invention.

FIG. 1 shows a beam limiting unit 1 comprising a leadscrew 2, having a right-hand thread extending from point A to point O and a left-hand thread extending from point O to point B. A first nut 3 engages the right-hand thread and moves on the right-hand thread; a second nut 4 engages the left-hand thread and moves on the left-hand thread. The beam limiting unit 1 further comprises a first blade 5 attached to the first nut 3, and a second blade 6 attached to the second nut 4. The first nut 3 is further provided with a pin 7 extending through a slot 8 machined in blade 5. A friction device (not shown), for instance a spring disposed between pin 7 and blade 5, presses the blade 5 against the nut 3. The beam limiting unit 1 is finally also provided with a first stop 10 and a second stop 11, which both delimit the motion path of blade 5. An actuator 12 drives the leadscrew 2.

As a whole, pin 7 and slot 8 form an uncoupling system 9 which uncouples the movement of actuator 12 and the movement of blade 5, in particular the movement of nut 3 and blade 5.

FIG. 1 shows an aperture, having width W, formed by the internal edges of blades 5 and 6, and having an axis of symmetry S.

It should be noted that the beam limiting unit 1 form the aperture of the X-ray imaging system in most cases. There might also be X-ray imaging system where the beam limiting unit 1 is just one of the baffles along the X-ray path and that the aperture of the X-ray imaging system is formed by another beam limiting unit 1.

Actuator 12 moves leadscrew 2 clockwise or anti-clockwise, pushing away or drawing closer, symmetrically and at the same time, the two nuts 3 and 4. On nut 3 pin 7 is fixed; pin 7 slides in slot 8 machined in blade 5. Blade 5 is secured to nut 3 through the friction device. The presence of the friction device allows a more controlled sliding of blade 5 on nut 3.

Blade 6 is integral with nut 4.

Figure 2:
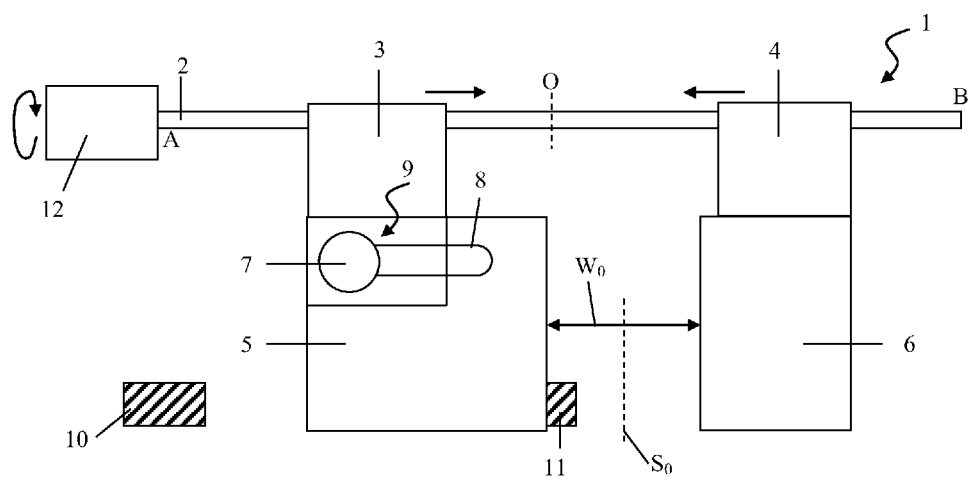
FIG. 2 a schematic view of the beam limiting unit when blades are approaching to each other (Step O)
Figure 2A:
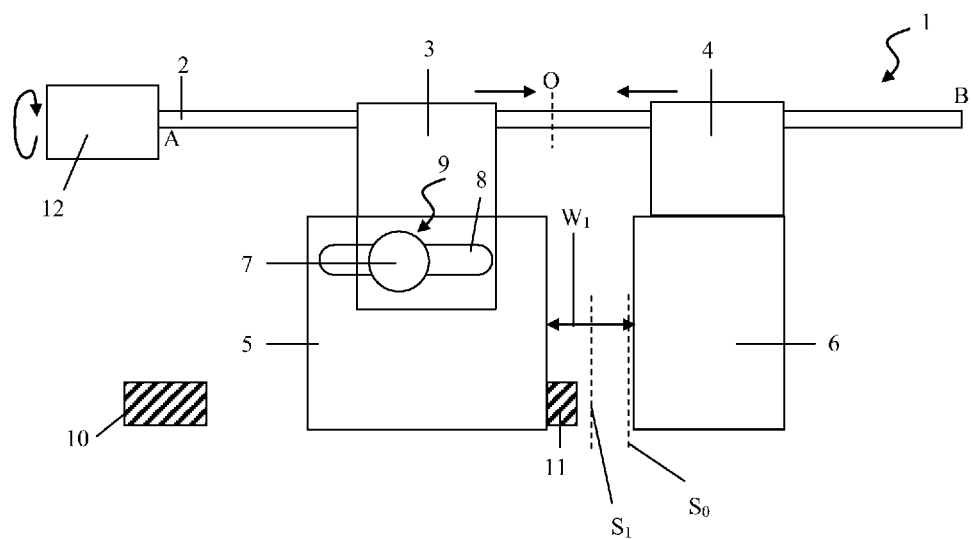
FIG. 2A a schematic view of the beam limiting unit during the setting of the symmetry axis of the aperture (Step A)
Figure 2B:
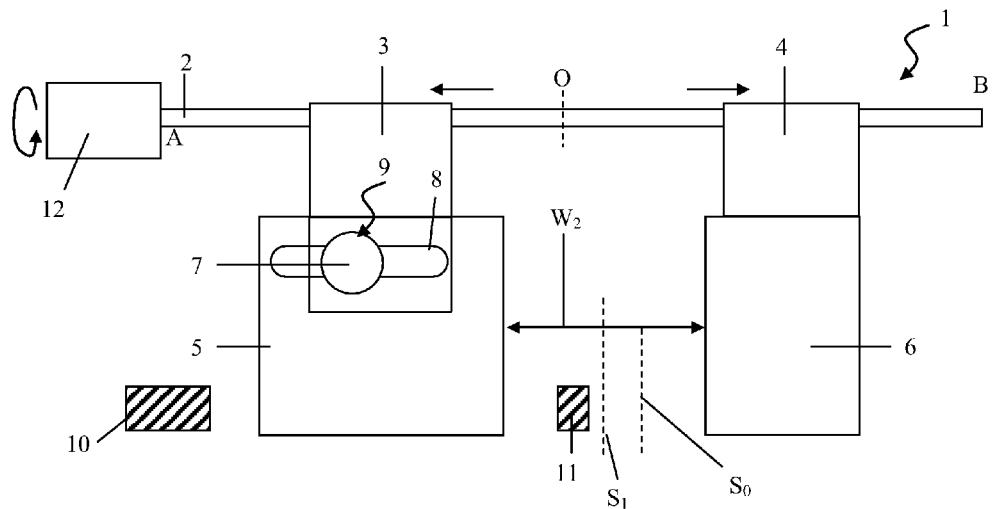
FIG. 2B a schematic view of the beam limiting unit during the setting of aperture width (Step B)
Figure 2C:
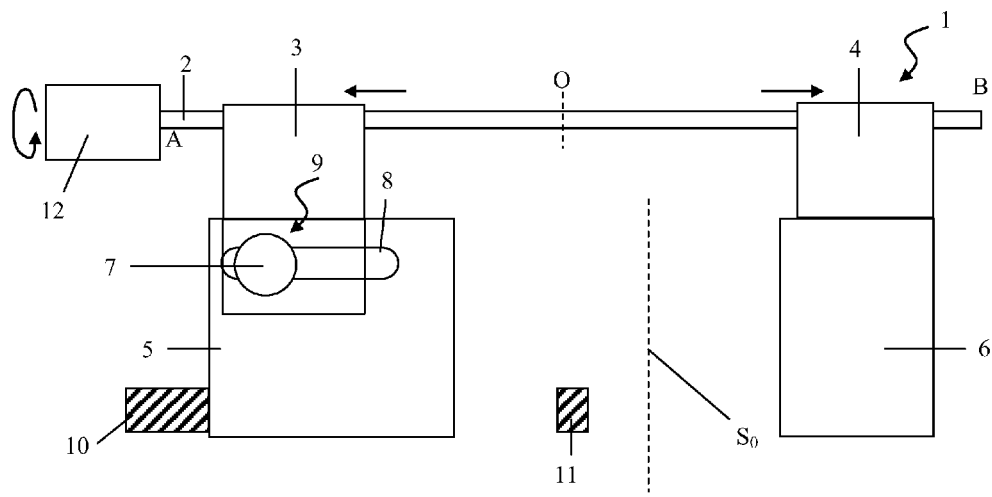
FIG. 2C a schematic view of the beam limiting unit during reset (Step C)

In the following, the operation of a beam limiting unit 1 will be described. For better clarity, the operation is subdivided into steps illustrated by FIGS. 2.

O) Step O: blades are drawn nearer and close

Actuator 12 rotates leadscrew 2. The two nuts 3, 4 are drawn nearer to each other, approaching the two blades 5 and 6. Blade 6 is integral with nut 4, therefore any movement of nut 4 entails a corresponding movement of blade 6. Blade 5 is secured with nut 3 through the friction device and pin 7, therefore, in this step, a movement of nut 3 entails a corresponding movement of blade 5. At a certain point blade 5 abuts stop 11. When blade 5 abuts stop 11, an aperture having width $W_0$ forms between the internal edges of the two blades 5 and 6. In the aperture having width $W_0$, $S_0$ represents the initial axis of symmetry dividing it into two symmetrical parts.

A) Step A: setting of the axis of symmetry of the aperture (shifting step)

Actuator 12 continues to rotate leadscrew 2 in the same direction as in Step O: the two nuts 3 and 4 continue approaching each other. Blade 6 is integral with nut 4, therefore any movement of nut 4 entails a corresponding movement of blade 6.

Blade 5 is pushed by stop 11 in a direction contrary to the movement of nut 3. This thrust is greater than the friction exerted by the friction device, therefore blade 5 can slide on the underlying nut 3. The movement is guided by pin 7 along slot 8.

Now an aperture having width $W_1$ has formed; $S_1$ represents the axis of symmetry of this second aperture (different from $S_0$). Differentiating position $S_1$ from position $S_0$ is possible as much as allowed by the width of slot 8.

Actuator 12 continues to rotate the leadscrew 2 until $S_1$ arrives at the desired position (setting of the axis of symmetry of the aperture).

B) Step B: setting the width of the aperture (adjustment step)

Actuator 12 reverses the rotation of leadscrew 2 with respect to step A. The two nuts 3 and 4 move away from each other in a symmetrical manner.

Blade 6 is integral with nut 4, therefore any movement of nut 4 entails a corresponding movement of blade 6.

Blade 5 is secured to nut 3 through the friction device and pin 7, and there is no other thrust, therefore, in this phase, the movement of nut 3 corresponds to the movement of blade 5.

Now an aperture having width $W_2$ has been formed; $S_1$ represents the axis of symmetry of this second aperture; $S_1$ remains unaltered with respect to Step A in that, in this phase, the withdrawal of the two blades 5 and 6 from $S_1$ is symmetrical.

Actuator 12 continues to rotate the leadscrew 2 until the aperture reaches the desired width $W_2$ between the two blades.

At this point, the aperture of the beam limiting unit has the desired width $W_2$ and the symmetry axis $S_1$ is at the desired position. It should be noted that the present invention reaches the desired setting with only two steps. Should it be necessary to modify the symmetry axis, the beam limiting unit 1 must be reset, that is the symmetry axis S of the aperture must be restored to its initial position $S_0$.

C) Step C: restoring of the position of the axis of symmetry $S_0$ (restoration step)

Actuator 12 rotates leadscrew 2 so as to push away blades 5 and 6 from each other. The two nuts 3 and 4 are withdrawn in a symmetrical way.

Blade 6 is integral with nut 4, therefore any movement of nuts 4 entails a corresponding movement of blade 6.

Blade 5 is secured to nut 3 through the friction device and pin 7, and there are no other thrusts, therefore, in this phase, the movement of nut 3 corresponds to the movement of blade 5.

At a certain point blade 5 abuts stop 10.

Blade 5 is pushed by stop 10 in a direction contrary to the movement of nut 3. This thrust is greater than the friction exerted by the friction device, therefore blade 5 can slide on the underlying nut 3. The movement is guided by pin 7 on slot 8.

Actuator 12 continues to turn until pin 7 arrives at the slot end, restoring the initial arrangement of the beam limiting unit 1.

A beam limiting unit without stop 11 can also be built. In this case, the operation is slightly modified, in that the role of stop 11 is performed by the abutment of the two blades 5 and 6 for setting the symmetry axis of $S_1$ (Step A). Once axis $S_1$ is set, the two blades 5 and 6 move away from each other forming an aperture having the desired width W (Step B). The embodiment without stop 11 has the advantage of allowing to set the symmetry axis S of the aperture having width W with a greater freedom.

Nonetheless, the beam limiting unit 1 having stop 11 is the preferred embodiment, in that the setting of point $S_1$ is quicker as blade 5 abuts stop 11 without the need to contact blade 6.

Instead of the stops 10 and 11, the motion of the blade 5 can also be impeded by other mechanical means such as braking, clutching or latching means or other mechanical, electrodynamic or hydrodynamic means which impede and in particular stop the motion of the blade 5 starting from a given point along the motion path of nut 3 and therefore blade 5.

In a modified embodiment, the position of the symmetry axis S can also be set by abutting the external stop 10 instead of the internal stop 11. Vice versa the inner stop 11 can also be used for the restoration step.

In the embodiments described herein, both blades 5, 6 are directly linked to the actuator 12 by separate force transmission chains. The blade 5 is linked to the actuator 12 by means of the leadscrew 2, the first nut 3 and the uncoupling system 9 formed by the pin 7, slot 8 and the friction device. The blade 6 is linked to the actuator 12 by means of the leadscrew 12 and the second nut 4. By these separate force transmission chains—one between actuator 12 and blade 5, and the other one between actuator 12 and blade 6—the forces generated by the actuator 12 are transmitted to both blades 5 and 6 directly and simultaneously resulting in both a speedy positioning of the central beam and a swift adjustment of the width W of the aperture.

Moreover, should a rectangular aperture be needed, having a ratio between two adjacent sides very different from 1, realising a perfectly rectangular aperture, wherein the edges of blades 5 and 6 are parallel would be costly and complex using a beam limiting unit without stop 11. The presence of stop 11 allows to get an aperture wherein the opposed sides are parallel, thanks to the fact that the presence of stop 11 recovers the clearance of blade 5 departing from a window having a non-rectangular shape. The dimensional precision of the aperture is important for the certification of the medical device. This problem in many prior art devices is overcome by limiting the fan X-ray beam with a beam limiting unit having a fixed profile, wherein the dimensions of the beam cannot be varied.

Obviously beam limiting unit 1 can be provided with detection devices known in the art (photoelectric cells, microswitches, etc.) for detecting the stop positions of the various moving elements.

Figure 3:
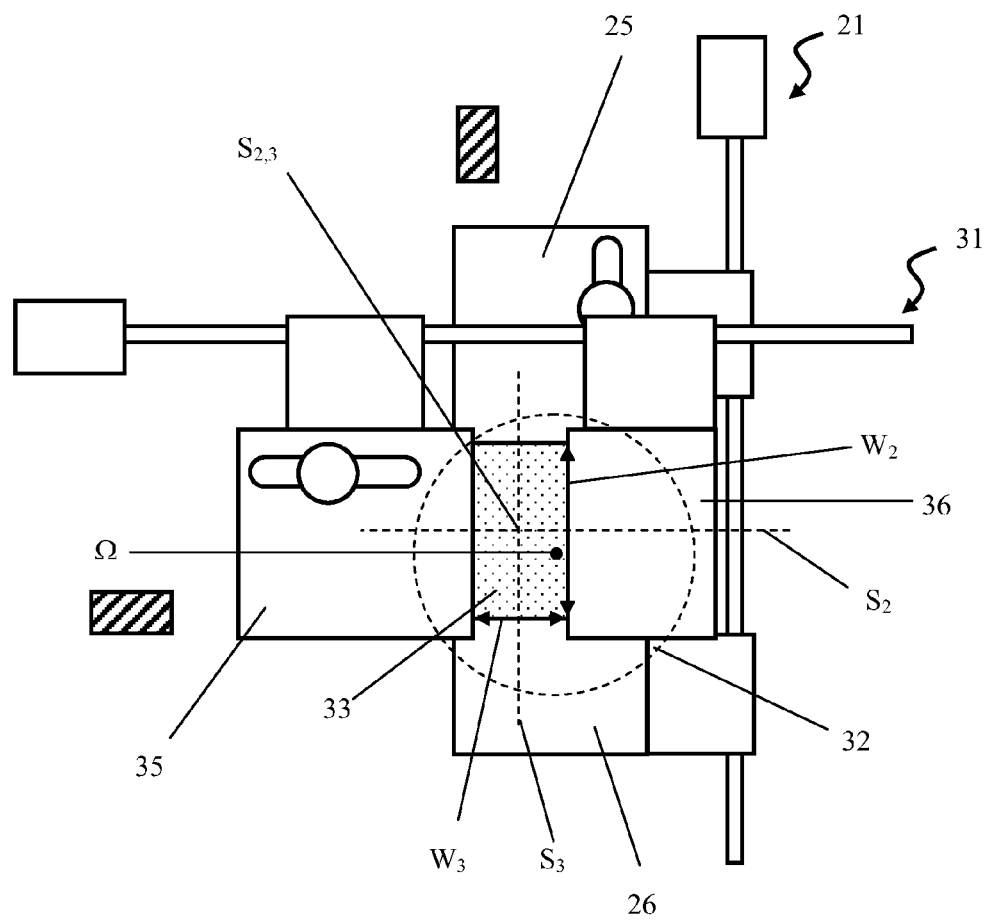
FIG. 3 a schematic view of two superimposed beam limiting units.

FIG. 3 shows two beam limiting units 21 and 31, one superimposed on the other with an angle of 90°. Beam limiting unit 21 limits an aperture having width $W_2$ and axis of symmetry $S_2$, while beam limiting unit 31 limits an aperture having width $W_3$ and axis of symmetry $S_3$. The symmetry axes $S_2$ and $S_3$ are aligned at right angle. FIG. 3 shows that the X-ray beam emitted by X-ray tube has a conical shape and therefore a circular cross section 32 having centre $\Omega$, which is transformed to a quadrilateral shape 33 thanks to the superimposition of the two beam limiting units 21 and 31, formed by the couple of blades 25 and 26 and the couple of blades 35 and 36, respectively.

FIG. 3 shows what was stated in the introduction: point $S_{2,3}$, the intersection of the symmetry axis $S_2$ of beam limiting unit 21 and of the symmetry axis $S_3$ of beam limiting unit 31 does not coincide with central point $\Omega$ of the circular cross section of the conical beam emitted by the X-ray tube.

Different shapes of the aperture can be obtained using blades having different shapes and/or superimposing two beam limiting units with an angle different from 90°, which makes the beam limiting unit of the present invention suitable for any radiographic apparatus.

The beam limiting unit of the present invention finds a particularly advantageous application in the technical field of the extraoral dental radiology.

In the following, reference will be made to extraoral radiographic apparatuses performing panoramic radiographies, cranial teleradiography and volumetric radiographies of the facial skeleton with cone beam technique. All these types of radiographies are well known in dental radiography.

Panoramic radiography (in some cases also called orthopantomography) produces a radiographic image of a curved plan approximating patient jaws, with blurring of the anatomical structures laying outside a narrow layer around the predesigned curved plane. Usually the acquisition of a panoramic radiography occurs with a fan beam X-ray beam, that is with a beam limiting unit producing a rectangular aperture wherein the ratio between two adjacent sides is very different from 1.

Teleradiography is a projective radiographic technique, producing radiographic images of the skull or of other anatomical areas from different projections, with minimum magnification and geometrical distortion. Usually two perspectives are represented, latero-lateral and anteroposterior. The acquisition of a teleradiography can occur with two different modalities:

1) with a fan shaped X-ray beam, that is with the beam limiting unit producing a rectangular aperture wherein the ratio between two adjacent sides is very different from 1;

2) in one-shot modality, that is with a beam limiting unit producing a quadrangular aperture having the same proportions of the X-ray detector. In case 2) the ratio between adjacent sides of the rectangle is closer to 1 than in case 1).

Cone beam volumetric radiography (also known as CBCT) is the acquisition, from different projection angles, of a series of bidimensional radiographic images which will be processed post-acquisition to reconstruct tridimensional volumes. In this case, the aperture can be rectangular, square or even circular, according to the X-ray detector. In addition to the above-mentioned needs, when performing a CBCT volumetric radiography, interposing a filter between the X-ray tube and the patient might be necessary in order to improve the reconstruction quality of bones, and decreasing the quantity of harmful soft X-rays.

The beam limiting unit of the present invention finally allows to add or remove an X-ray filter, which can be positioned upstream or downstream of the beam limiting unit itself, as shown in FIG. 4.

Figure 4A:
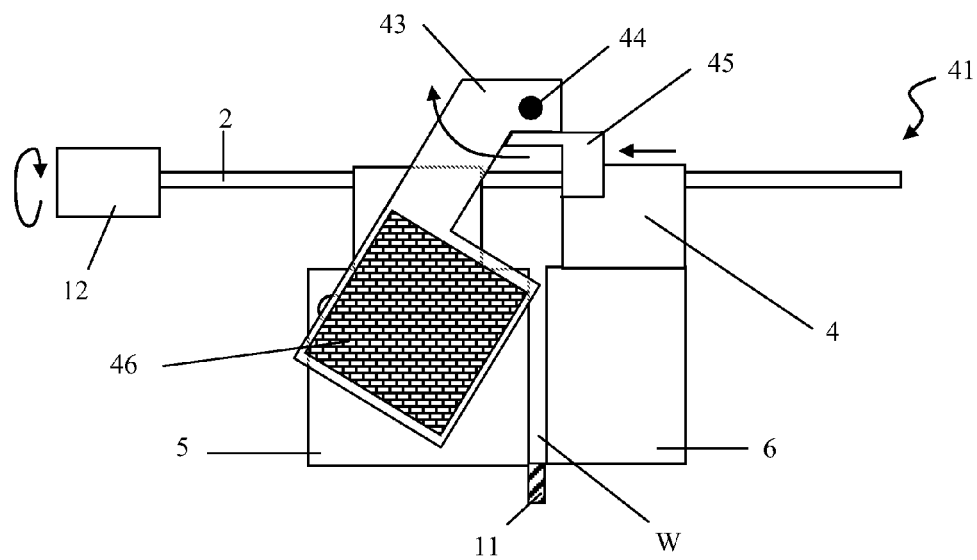
FIG. 4A a schematic view of the beam limiting unit without filter.

FIG. 4A shows beam limiting unit 41 in its setting for acquiring a panoramic radiography: as can be seen, the aperture having width W is of a rectangular shape wherein the ratio between adjacent sides is very different from 1, conferring to the X-ray beam the typical fan shape. During the acquisition of a panoramic radiography the X-ray beam does not need further filtration.

Figure 4B:
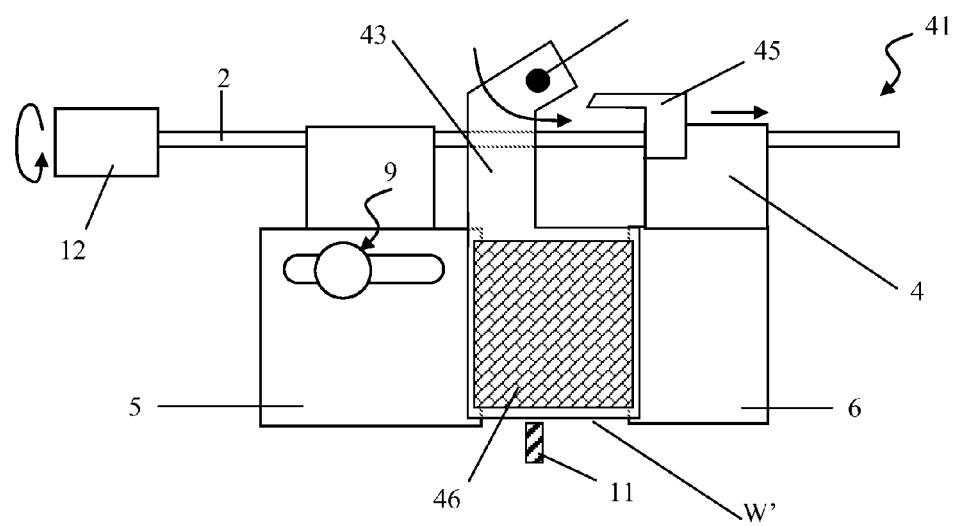
FIG. 4B a schematic view of the beam limiting unit with filter.

FIG. 4B shows instead beam limiting unit 51 during the acquisition of a CBCT volumetric radiography, which needs a supplementary filtration of X-ray beam emitted by X-ray tube. To this aim, on the X-ray path, a filter 46 is interposed, which can be indifferently positioned upstream or downstream beam limiting unit 41.

The superimposition of the filter to the aperture formed by collimation unit 41 is linked to the position of nut 4. As a matter of fact, on nut 4 a cam 45 is fixed which pushes arm 43, supporting filter 46, so that it can rotate around pin 44. When blades 5, 6 are at short distance (FIG. 4A), the filter 46 is pushed so as to remove it from aperture; when blades 5, 6 are sufficiently far away from each other (FIG. 4B), a spring (not shown) returns arm 43, so that filter 46 is superimposed on the aperture.

Using suitable dimensions of filter 46, arm 43 and cam 45, it is possible that, given a pre-set width W of aperture, filter 46 covers it completely and that, given another pre-set W' of the aperture, the filter is completely removed from the X-ray path. Although the beam limiting unit 1 can form apertures having any width W in a continuous mode, in reality, when positioned inside an extraoral radiographic apparatus, the effectively used apertures are only a discrete number, having a pre-defined width W.

LIST OF REFERENCE NUMERALS 1 beam limiting unit
2 leadscrew
3 first nut
4 second nut
5 first blade
6 second blade
7 pin
8 slot
9 uncoupling system
10 first stop
11 second stop
12 actuator
21 first beam limiting unit
25 first blade of beam limiting unit 21

26 second blade of beam limiting unit 21
31 second beam limiting unit
32 circular section of the X-ray beam impinging on beam limiting unit
33 aperture
35 first blade of beam limiting unit 31
36 second blade of beam limiting unit 31
41 beam limiting unit with filter
43 arm supporting filter
44 pin
45 cam
46 supplementary filter

The invention claimed is:

1. Method for limiting an X-ray beam, wherein the X-ray beam is limited by a limiting unit (1) comprising at least two blades (5, 6) approaching each other or moving away from each other to adjust the width of a space between the blades (5, 6), the two blades (5, 6) being driven by an actuator (12) linked to both blades (5, 6)
characterized by
shifting the position of a symmetry axis (S) of the space between the blades (5, 6) by changing the distance between the blades (5, 6) and by impeding the motion of one blade (5) in comparison with the motion of the other blade (6) resulting in an asymmetric motion of the blades with respect to an initial position of the symmetry axis (S), and
adjusting the desired width (W) of the space between the blades (5, 6) by an unimpeded symmetric motion of the blades (5, 6) with respect to the position of the symmetry axis (S) set in the shifting step.

2. Method for limiting an X-ray beam according to claim 1, further comprising a restoration step for shifting the symmetry axis of the opening to the initial position of the symmetry axis (S) by changing the distance between the blades (5, 6) in a direction opposite to the direction used in the shifting step and by impeding the motion of the one blade (5) resulting in an asymmetric motion of the blades (5, 6) with respect to the initial position of the symmetry axis (S).

3. Method for limiting an X-ray beam according to claim 1, wherein the motion of the one blade (5) is impeded by using at least one stop (10, 11) disposed in the motion path of the one blade (5) and by using an uncoupling system (9), which allows a relative motion of the one blade (5) with respect to a holder engaged with the actuator (12).

4. Method for limiting an X-ray beam according to claim 1, wherein the width (W) of the space is varied during X-ray emission for the acquisition of a radiography.

5. Method for limiting an X-ray beam according to claim 1, further comprising a filter (46) which is superimposed on the space between the blades (5, 6) by a mechanism (43-45), which transfers the filter (46) to the space when the width (W) of the space exceeds a predetermined dimension.

6. Apparatus (1) for limiting an X-ray beam on opposite sides of the X-ray beam comprising:
two blades (5, 6) disposed on opposite sides of the X-ray beam and having inner edges, which delimit the X-ray beam on said opposite sides,
an actuator (12) linked to both blades (5, 6) and configured to move the blades in an approaching direction to reduce the space between the inner edges of the blades (5, 6), and configured to move the blades in a withdrawing direction to enlarge the space between the inner edges of the blades (5, 6), and
a stop (11) configured to impede the motion of one of the blades (5)
characterized in that
the actuator (12) is configured, when the motion of the one blade (5) is impeded by the stop (11), to shift the position of a symmetry axis (S) of a space between the inner edges of the blades (5, 6) by asymmetric motion of the blades (5, 6) with respect to an initial position of the symmetry axis (S), and
the actuator (12) is configured, when the one blade is not impeded by the stop (11), to adjust a desired width (W) of the space between the blades (5, 6) by symmetric motion of the blades (5, 6) with respect to the position of the symmetry axis (S).

7. Apparatus (1) for limiting an X-ray beam according to claim 6, wherein the motion of the one blade (5) in the approaching direction and/or withdrawing direction is impedable by an abutment and wherein the abutment is the inner edge of the other blade (6) or the stop (11) disposed in a motion path of the one blade (5), and wherein the stop (11) abuts the one blade (5) in the withdrawing direction.

8. Apparatus (1) for limiting an X-ray beam according to claim 6, further comprising a filter (46) movable by a mechanism (43-45) between a first position, in which the filter (46) superimposes the space between the blades (5, 6), and a second position, in which the filter (46) is placed at a location beside the space between the blades (5, 6), wherein the mechanism (43-45) moves the filter (46) depending on the distance between the blades (5, 6) or the position of one of the blades (5, 6).

9. System for limiting an X-ray beam comprising two superimposed limiting units (21, 31) according to claim 6, whose respective blades (25, 26, 35, 36) delimit the X-ray beam on four sides.

10. System for limiting an X-ray beam according to claim 9, wherein a central point ($\Omega$) of the delimited X-ray beam lies in a position different from a point ($S_{2,3}$) formed by an intersection of symmetry axes ($S_2$, $S_3$) of the spaces between respective opposing blades (25, 26, 35, 36).

* * * * *